United States Patent [19]

Hanna et al.

[11] Patent Number: 4,601,894
[45] Date of Patent: Jul. 22, 1986

[54] CONTROLLED RELEASE DOSAGE FORM COMPRISING ACETAMINOPHEN, PSEUDOEPHEDRINE SULFATE AND DEXBROMPHENIRAMINE MALEATE

[75] Inventors: Gayda Hanna, Berwyn, Pa.; Winston A. Vadino, Bridgewater, N.J.

[73] Assignee: Schering Corporation, Kenilworth, N.J.

[21] Appl. No.: 718,036

[22] Filed: Mar. 29, 1985

[51] Int. Cl.$^4$ ............................ A61K 9/22; A61K 9/26
[52] U.S. Cl. ...................................... 424/19; 424/22; 514/781
[58] Field of Search ................... 424/19, 22; 514/781

[56] References Cited

U.S. PATENT DOCUMENTS

| | | | |
|---|---|---|---|
| 3,065,143 | 11/1962 | Christenson et al. | 424/19 |
| 4,226,849 | 10/1980 | Schor | 514/781 |
| 4,259,314 | 3/1981 | Lowry | 514/781 |
| 4,369,172 | 1/1983 | Schor et al. | 514/781 |
| 4,389,393 | 6/1983 | Schor et al. | 514/781 |

OTHER PUBLICATIONS

A. Ph. A. Handbook of Non-Prescription Drugs 6th Ed. (1979) pp. 73-114, Cold and Allergy Products.
PDR 1984 38th Ed. Physicians Desk Reference pp. 214, 215, 216, 301, 302, 305, 307, 309, 326, 327, 972, 973, 993, 1176, 1385, 1758, 1759, 1802, 1803.

Primary Examiner—Shep K. Rose
Attorney, Agent, or Firm—Anita W. Magatti; Stephen I. Miller

[57] ABSTRACT

The invention relates to a controlled release dosage form comprising three actives: acetaminophen, psueudoephedrine sulfate and dexbrompheniramine maleate.

13 Claims, No Drawings

CONTROLLED RELEASE DOSAGE FORM COMPRISING ACETAMINOPHEN, PSEUDOEPHEDRINE SULFATE AND DEXBROMPHENIRAMINE MALEATE

SUMMARY OF THE INVENTION

The present invention relates to an oral controlled release matrix dosage form which combines three pharmaceuticals, acetaminophen, pseudoephedrine or a pharmaceutically acceptable salt thereof and dexbrompheniramine or a pharmaceutically acceptable salt thereof, a polymer, and excipients.

BACKGROUND OF THE INVENTION

Acetaminophen is a well known analgesic and antipyretic which reduces the discomfort and fever due to colds and other viral infections.

Pseudoephedrine and pharmaceutically acceptable salts thereof, e.g. the sulfate and the hydrochloride, are well known decongestants which restore freer breathing by shrinking nasal passages and promote sinus drainage in those suffering from colds, allergies or sinusitis.

Dexbrompheniramine and pharmaceutically acceptable salts thereof, e.g. the maleate, are well known antihistamines which provide relief of the pruritis, rhinitis and sneezing associated with colds and allergies.

Controlled release dosage forms are well known, including matrix tablet systems incorporating active ingredients, lubricants, binders, fillers and other excipients, wherein the binders may be hydrophillic, hydrophobic or water insoluble polymers. See for example U.S. Pat. No. 4,389,393. However, controlled release dosage forms which combine two actives are not common, and no controlled release dosage forms combining three actives in a single uniform dosage form are known. The mechanism by which controlled release dosage forms act to dispense the active ingredients over a period of time hve been described at length in the literature. See for example Manford Robinson, Chapter 14, "Sustained Action Dosage Forms", *The Theory and Practice of Industrial Pharmacy*, 2nd. ed., ed. L. Lachman, H. Lieberman and J. Kanig (Philadelphia; Lea & Febiger, 1976).

DETAILED DESCRIPTION OF THE INVENTION

The controlled release dosage form which is the subject of this invention represents a novel advancement of the art since it combines three active ingredients, acetaminophen, pseudoephedrine or a pharmaceutically acceptable salt thereof, preferably pseudoephedrine sulfate, and dexbrompheniramine or a pharmaceutically acceptable salt thereof, preferably dexbrompheniramine maleate, in a single long-acting tablet. While antihistamines and decongestants have been combined in controlled release tablets, and while antihistamines, decongestants and analgesics have been combined in 2-layer tablets or have been separately microencapsulated and combined in continuous action capsules, the present invention relates to a surprisingly simple combination of three actives in a single matrix, from which matrix each active component is released at an appropriate rate to provide the desired activity over a period of 2-14, preferably 8-12 hours.

The components of the matrix are preferably chosen so that a dosage regimen in which two tablets are administered every 12 hours may be maintained.

It is most unexpected that each active component is released from the matrix at its desired rate despite the difference in solubilities between the actives in gastric or aqueous media, indicating that different mechanisms of drug release, i.e. diffusion through, and erosion of the hydrated layer, are occurring simultaneously. Another unexpected feature is that the differences in dosage size to not affect release of the actives. That is, acetaminophen, pseudoephedrine and dexbrompheniramine may be present at a ratio of 200:20:1, for example, and the desired release rates are still obtained. It is also unexpected that three actives with significantly different biological half-lives should each demonstrate its own pharmacological profile when combined is a sustained release single dosage form.

The specific preferred combination of actives of the invention, i.e. acetaminophen, pseudoephedrine sulfate and dexbrompheniramine maleate, presents an advantage to the cold or allergy sufferer by providing a single medication with antihistaminic, decongestant and analgesic properties. Moreover, it is apparent that in addition to the well known pharmacological advantages of a controlled release formulation in general (e.g. more constant blood levels of the drugs), the dosage form of the present invention is easier and more economical to manufacture than microencapsulated or 2-layered dosage forms.

Although the three actives and a polymer must always be present in the dosage form of the invention, the concentrations of the actives and polymer may vary. For the filler and other excipients, the nature as well as the concentration of the component may vary.

Acetaminophen may be present at from 400 to 750 mg/tablet, preferably 500 mg/tablet. Pseudophedrine sulfate may be present at from 15 to 75 mg/tablet, preferably 60 mg/tablet. Dexbrompheniramine maleate may be present in the range of 1 to 5 mg/tablet, with 3 mg/tablet being preferred.

While a number of polymers might be used as the binder for the matrix, this invention particularly contemplates the use of water-soluble hydroxypropyl methylcellulose (HPMC) ethers and the water-insoluble ethylcellulose. A variety of HPMC ethers is commercially available, for example Dow's METHOCEL K, HPMC (USP 2208), METHOCEL E, HPMC (USP 2910), and METHOCEL F, HPMC (USP 2906). See "Formulating Sustained Release Pharmaceutical Products with Methocel" (The Dow Chemical Co., 1982). The faster-hydrating USP 2208 is preferred.

The total polymer content represents 1–8% by weight of the dosage form, and of the polymer weight, 100–60% may be HPMC and 0–40% may be ethylcellulose. A preferred range for the total amount of polymer present in the dosage form is 6–6.5%. In a preferred embodiment, HPMC is the only polymer used, i.e. 100% HPMC, with 100% HPMC USP 2208 being more preferred.

Also present in the matrix are one or more fillers such as dibasic calcium phosphate dihydrate or lactose, with dibasic calcium phosphate dihydrate being preferred. The filler is present in an amount of 10–13% of the total dosage form weight, with about 12% being preferred.

When the weight of the polymer component is varied, corresponding variations in the filler weight are made in order to maintain constant tablet weight and controlled release profile.

The matrix also contains one or more lubricating agents, e.g. stearic acid, magnesium stearate, calcium stearate, waxes, polyethylene glycol, or magnesium lauryl sulfate, present in an amount of 1–3% of the total dosage form weight. A preferred embodiment comprises 0.9–1.7% stearic acid and 0.25 to 0.78% magnesium stearate.

Other excipients, such as disintegrating agents, coloring agents and flavorings may be added at the discretion of those skilled in the art.

The above components are combined to form the matrix and formed into tablets by conventional means (see Example 1). The tablets may be used as is, but are preferably coated by techniques well known in the art. An example of such a tablet coating is shown in Example 1.

The following examples describe typical batch formulas of the controlled release dosage forms of this invention.

EXAMPLE 1

| Tablet Cores Ingredients | Approximate g/Batch |
| --- | --- |
| Acetaminophen USP 90% (I)* | 66,667 |
| Pseudoephedrine Sulfate USP (II) | 7,200 |
| Dexbrompheniramine Maleate USP (III)** | 369 |
| Hydroxypropyl Methylcellulose 2208 USP | 5,760 |
| Dibasic Calcium Phosphate Dihydrate USP | 11,324 |
| Stearic Acid NF | 1,200 |
| Magnesium Stearate NF | 480 |
| Purified Water USP (evaporates) | — |
| Alcohol 3A SD (evaporate) | — |
| Approximate Batch Weight (g) | 93,000 |
| Approximate Core Yield (cores) | 120,000 |

*Equivalent to 60,000 g of Acetaminophen.
**Up to a 5% manufacturing overcharge may be added with compensating adjustments in the core weight, the amount of filler or both.

Method of Manufacture

Blend I, II, dicalcium phosphate dihydrate and hydroxypropyl methylcellulose for 5–30 minutes in a suitable mixer. Dissolve III in hydroalcoholic mixture and use it to granulate the powder blend. Dry and mill the granulation using suitable size screen. Add remaining ingredients and blend for 3–15 minutes. Compress into suitable size tablets.

| Tablet Coating: Ingredients | Approximate Grams/Batch |
| --- | --- |
| Hydroxylpropyl Methylcellulose 2910 or 2906 USP | 18,000 |
| Polyethylene glycol 3350 NF | 420 |
| Methylparaben NF | 20 |
| Propylparaben NF | 14 |
| Purified Water USP (evaporates) | (1) |
| Coloring Agent | (2) |

(1) Sufficient amounts of Purified Water are used as required in the coating process.
(2) An appropriate amount of a coloring agent (e.g. color dispersion solids) may be added.

Method of Manufacture

Prepare polymer solution using standard methods. Combine polymer solution with color dispersion and sufficient water. Coat tablets with colored polymer solution and polish the coated tablets using standard procedures.

EXAMPLE 2

| Tablet Core: Ingredients | Approximate g/Batch |
| --- | --- |
| Acetaminophen USP | 60,000 |
| Pseudoephedrine sulfate USP | 7,200 |
| Dexbrompheniramine Maleate USP* | 369 |
| Hydroxypropyl Methylcellulose | 6,300 |
| Ethylcellulose NF | 4,500 |
| Dicalcium Phosphate Dihydrate USP | 10,080 |
| Stearic Acid NF | 1,140 |
| Magnesium Stearate NF | 420 |
| Purified Water USP (evaporates) | — |
| Alcohol 3A 5D (evaporates) | — |
| Approximate Batch Weight (g) | 90,009 |
| Approximate Core Yield (cores) | 120,000 |

*Up to a 5% manufacturing overcharge may be added with compensating adjustments in the core weight or amount of filler or both.

Method of Manufacture

Blend I, dicalcium phosphate dihydrate, II and hydroxypropyl methylcellulose in suitable mixer for 5–30 minutes. Dissolve III and ethylcellulose in 3A alcohol and use it to granulate powder blend. Dry and mill granulation using suitable size screen. Add remining ingredients and blend for 3–15 minutes. Compress into suitable size tablets.

The tablet cores may be coated in a manner similar to that described in Example 1.

We claim:

1. An oral dosage form comprising an analgesic-effective amount of acetaminophen, an amount of pseudoephedrine or a pharmaceutically acceptable salt thereof effective in reducing nasal congestion, and an antihistaminic-effective amount of dexbrompheniramine or a pharmaceutically acceptable salt thereof in a uniform matrix comprising a controlled release carrier comprised of a polymer selected from hydroxypropyl methylcellulose ethers or a combination of polymers selected from hydroxypropyl methylcellulose ethers and ethylcellulose.

2. A dosage form of claim 1 comprising 400 to 750 mg of acetaminophen, 15 to 75 mg of pseudoephedrine sulfate, and 1 to 5 mg of dexbrompheniramine maleate.

3. A dosage form of claim 2 comprising 500 mg acetaminophen, 60 mg pseudoephedrine sulfate and 3 mg dexbrompheniramine maleate.

4. A dosage form of claim 1 wherein the carrier comprises a polymer, wherein the polymer is comprised of 100–60% hydroxypropyl methylcellulose ethers and 0–40% ethylcellulose, one or more lubricants selected from stearic acid, magnesium stearate, calcium stearate, waxes, polyethylene glycol and magnesium lauryl sulfate, and one or more fillers selected from the group consisting of dibasic calcium phosphate dihydrate and lactose.

5. A dosage form of claim 4 wherein the total polymer weight represents 1–8% of the total dosage form weight, the total binder weight represents 11–13% of the total dosage form weight, and the total lubricant weight represents 1–3% of the total dosage form weight.

6. A dosage form of claim 5 wherein the polymer is 100% hydroxypropyl methylcellulose.

7. A dosage form of claim 5 wherein the polymer is 100% hydroxypropyl methylcellulose USP 2208.

8. A dosage form of claim 5 wherein the filler is dibasic calcium phosphate dihydrate.

9. A dosage form of claim 5 wherein the lubricants are stearic acid and magnesium stearate.

10. A dosage form of claim 5 comprising 1-8% hydroxypropyl methylcellulose, 10-13% dibasic calcium phosphate dihydrate and 1-3% of a combination of stearic acid and magnesium stearate.

11. A dosage form of claim 10 comprising 1-8% hydroxypropyl methylcellulose USP 2208.

12. A dosage form of claim 11 comprising 400 to 750 mg acetaminophen, 15 to 75 mg pseudoephedrine sulfate and 1 to 5 mg dexbrompheniramine maleate.

13. A dosage form comprising 500 mg acetaminophen, 60 mg pseudoephedrine sulfate, 3 mg dexbrompheniramine maleate, 48 mg hydroxypropyl methylcellulose USP 2208, 95 mg dibasic calcium phosphate dihydrate, 10 mg stearic acid and 4 mg magnesium stearate in a uniform matrix.

* * * * *